(12) United States Patent
Perry

(10) Patent No.: US 12,680,072 B2
(45) Date of Patent: Jul. 14, 2026

(54) MYCOMATERIAL PROCESSING IN LIQUID MEDIUM

(71) Applicant: MycoWorks, Inc., Emeryville, CA (US)

(72) Inventor: Stephen Perry, Durham, NH (US)

(73) Assignee: MyCoWorks Denver, LLC, Georgetown, CO (US)

( * ) Notice: Subject to any disclaimer, the term of this patent is extended or adjusted under 35 U.S.C. 154(b) by 0 days.

(21) Appl. No.: 17/866,499

(22) Filed: Jul. 16, 2022

(65) Prior Publication Data

US 2023/0016412 A1     Jan. 19, 2023

Related U.S. Application Data

(60) Provisional application No. 63/222,511, filed on Jul. 16, 2021.

(51) Int. Cl.
*C12N 1/14*          (2026.01)
*C12M 1/00*          (2006.01)
(Continued)

(52) U.S. Cl.
CPC .............. *C12N 1/14* (2013.01); *C12M 23/06* (2013.01); *C12M 27/10* (2013.01); *C12M 29/14* (2013.01); *C12N 2513/00* (2013.01)

(58) Field of Classification Search
CPC ...... C12N 1/14; C12N 2513/00; C12M 23/06; C12M 27/10; C12M 29/14
See application file for complete search history.

(56) References Cited

U.S. PATENT DOCUMENTS 1,338,307 A * 4/1920 Krouse ................... C14C 15/00
                                                    68/144
8,227,225 B2 * 7/2012 Rocco ...................... C12N 1/14
                                                    428/411.1
(Continued)

FOREIGN PATENT DOCUMENTS

WO        2017151684 A1      9/2017
WO        2019226823 A1     11/2019
(Continued)

OTHER PUBLICATIONS

Vacuum Tumbler SIP-VT-500 Owner's Manual. Accessed Jul. 18, 2024 from Wayback Machine, web archives. URL first available Jan. 25, 2021. 15 pages total. Accessed from: https://web.archive. org/web/20210125042549/https://www.cmmachineservices.net/ download/e142b27a36588623aa9c5d01cab938a6_SIP-VT-500_ manual.pdf (Year: 2021).*
(Continued)

*Primary Examiner* — Aaron J Kosar
*Assistant Examiner* — Andrew T Moehlman
(74) *Attorney, Agent, or Firm* — Temmerman Law; Mathew J. Temmerman

(57)          ABSTRACT

A system and method for making a biopolymer-based fungal mat is described. The system includes a plurality of fresh fungal materials, a mass balance, a liquid chemical solution and a vacuum tumbler drum. The method comprises the steps of harvesting the plurality of fresh mycelium material and marking them for identification, then weighing the initial mass of the mycelium materials is carried out. The liquid chemical solution is decanted into the vacuum tumbler drum distributed with the mycelium material. Thereafter, vacuum is applied to the vacuum tumbler drum and the drum is rotated to ensure thorough mixing and refreshing of the liquid chemical solution at the mycelium surface. The process of vacuuming and rotating the drum is repeated and
(Continued)

the fungal mat is formed. The fungal mat is removed from the vacuum tumbler drum for draining away surface moisture thereon to provide a dried fungal mat.

5 Claims, 3 Drawing Sheets

(51) Int. Cl.
    *C12M 1/12*       (2006.01)
    *C12M 3/04*       (2006.01)

(56)              References Cited

U.S. PATENT DOCUMENTS

| | | | |
|---|---|---|---|
| 8,298,809 B2 | 10/2012 | Kalisz | |
| 2003/0220039 A1 | 11/2003 | Chen | |
| 2007/0283504 A1* | 12/2007 | Wegner | C14C 15/00 |
| | | | 8/94.19 R |
| 2018/0014468 A1* | 1/2018 | Ross | A01G 18/10 |
| 2020/0392341 A1 | 12/2020 | Smith et al. | |
| 2020/0399824 A1* | 12/2020 | Stewart | B01D 11/0203 |

FOREIGN PATENT DOCUMENTS

| | | | | |
|---|---|---|---|---|
| WO | WO-2020115690 A1 * | 6/2020 | ............. | C12N 11/12 |
| WO | 2020257320 A1 | 12/2020 | | |

OTHER PUBLICATIONS

Vision Abell Pty Ltd. Report "Feasibility study of hide and leather identification systems" M.668, published by Meat & Livestock Australia (MLA), Mar. 1995 (61 pages total); www.mla.com.au/research-and-development/reports/1995/feasibility-study-of-hide-and-leather-identification-systems/ (Year: 1995).*

"Proximal." Merriam-Webster.com Dictionary, Merriam-Webster, https://www.merriam-webster.com/dictionary/proximal. Accessed Jan. 21, 2025. Last Updated on Dec. 28, 2024. Three pages total. (Year: 2024).*

Vision Abell Pty Ltd. Report "Feasibility study of hide and leather identification systems" M.668, published by Meat & Livestock Australia (MLA), Mar. 1995 (61 pages total); <URL:www.mla.com.au/research-and-development/reports/1995/feasibility-study-of-hide-and-leather-identification-systems/> (Year: 1995).*

Kari Rodriguez, International Search Report for counterpart international patent application PCT/US22/37406; US Patent and Trademark Office, Oct. 5, 2022.

* cited by examiner

MYCOMATERIAL PROCESSING IN LIQUID MEDIUM

PRIORITY

The application claims priority from the U.S. provisional application with Ser. No. 63/222,511, which was filed on Jul. 16, 2021. The disclosure of that provisional application is incorporated herein as if set out in full.

BACKGROUND OF THE DISCLOSURE

Technical Field of the Disclosure

The present invention relates generally to systems and methods for applying liquid chemistry to fungal materials and objects thereof. More particularly to a system and a method for applying liquid chemistry to fungal materials and objects with variable shape, size, thickness, density, flexibility, and other predetermined qualities through post-growth processing in which thorough and complete chemical distribution is achieved.

Description of the Related Art

Liquid chemistries and application methods have been variously investigated as related to animal skins, micropolymers, fabrics, and the like. Such treated materials have been adapted for widespread use in many different applications, such as furniture, car interiors, and nonwoven sheets which can be made into a variety of materials including clothing, structural materials, disposable absorbent products, protective materials, and the like. A typical end product that is treated with liquid chemistries generally comprises a structurally homogenous composite structure, including in some instances, a structurally distinct interior structure.

The properties and applications of fungal materials are strongly linked to their morphology, structure and size. In some cases, fungal materials may form a composite with other materials such as cotton textiles and/or chitin nano-whiskers. Such composites can be used for various applications and are widely utilized in textiles, packaging and building materials. The properties of fungal materials may be controlled by various methods, including liquid chemical treatment. Said chemical treatment allows for control of multiple important parameters including tensile strength, tear strength, abrasion resistance, in addition to various chemical properties such as dye and oil distribution and fixation. Liquid chemistry treatment may also help to optimize how putrescible or stabilized a given fungal material may be in a given end product. At a microscopic scale, distinct chemical bonding arrangements may be available for liquid chemistry treatment of fungal materials when compared to collagen or similar materials (animal leathers are composed of collagen, which is an organic, fibrous material). Fungal materials, on the other hand, are primarily comprised of various polysaccharides and proteins, creating a molecularly-distinct organic fiber material with a distinct make-up of hydroxyl versus amine groups available for chemical reaction.

As applied to mycelium materials, a liquid chemistry treated fungal material may be comprised of natural or modified fungal proteins, carbohydrates, and nucleic acids. Fungal materials also generally comprise a network of interlocking branched hollow tubes called hyphae. As described above, hyphae contain a unique molecular compound called chitin. Chitin is also the main constituent in the shells of crustaceans and is the most abundant naturally occurring biopolymer other than cellulose. Chitosan is derived from chitin and can be formed by deacetylation of chitin. Chitosan is commercially available in a wide variety of molecular weights (e.g., 10-1,000 kDa) and usually has a degree of deacetylation ranging between 70% and 90%. Chitosan is used for a wide variety of purposes including plant care, cosmetics additives, food and nutrition supplements and medical care.

Filamentous fungi have the natural tendency to join together smaller pieces of branching, colonial hyphae into a larger constituent whole, assembling and weaving strands and sheets of tissues called mycelium. Mycelium can adhere to, and possibly engulf, any other materials it comes in contact with through the extension of hyphae that use neighbor sensing and searching functions as guidance in their exploration into space beyond sources of nutritional sustenance. Like cement and plaster, fungal tissue will bind, harden and set into a variety of solidified configurations through the natural biological functions of mycelial growth and self-adhesion. In some instances, fungal tissues can quickly be amplified to a large volume if provided with the appropriate living conditions. These conditions include the nutrients that might be available to the organism, the possible gas gradients within the growth environment and the humidity, light, and temperatures the organism might be exposed to as it takes form. Fungi are very sensitive to their surroundings, and by altering subtle factors it is possible to prompt their tissue to express a range of variably determined physical characteristics.

Fungi are very sensitive to chemicals present in their environment and have the ability to alter the directions and vigor of growth of expanding hyphae as demonstrated through chemotaxic avoidance or attraction. Fungi are also very sensitive to other stimuli in their environment and have the ability to alter directions and vigor of growth of expanding hyphae in response to gravitropic, thermotropic, thigmotropic, phototropic, and hydrotropic stimuli. A substrate colonized with fungal hyphae, if provided adequate enclosure and environmental controls, will in a matter of one to three days generate a layer of fungal hyphae growing from the top of said substrate that will expand into space as a layer in a fuzzy and undifferentiated manner. This undifferentiated layer of hyphae, if left to continue growing, will soon advance in development and differentiate into specialized tissues determined to become fruit bodies or other sporocarp-producing structures.

Cellulosic materials have been shown to be physically altered through application of liquid chemistry, fungal materials have enjoyed less success in being physically altered in the same way due to poor chemical distribution. The methods described herein achieve homogenous chemical distribution. Under optimized conditions, fungal composites may be altered through the application of liquid chemistries in order to exhibit equivalent or improved properties and characteristics as compared to animal skins and similar materials.

Various processes exist in the prior art that may be used in connection with the treatment of cellulosic materials. One such method uses mixing chitin and protein materials in a solution. This approach does not yield any improvement in the mechanical properties of mixture over the components, and typically produces an even weaker material due to the interaction of both polymers, which interferes with each other's molecular and crystal structure. Also, this method fails to provide a unique molecular structure for the liquid chemistry treated chitin-based fungal materials and their composites.

Another method describes controlling the fungal material utilizing aqueous liquid composition having low environmental load and poor chemical distribution. In this method, the physical properties of the cellulosic materials are altered due to various functions like electrical conductivity and hydrophilicity that are adhered on the base material. Also, this method does not enhance desired characteristics such as improved flexibility and tensile strength.

Therefore, there is thus a need for a safe and efficient system and method for controlling the properties of the fungal materials such as mycelium material. Such a needed method would provide a biopolymer-based fungal mat with well controlled mechanical and chemical properties. Further, such a system and method would successfully alter, preserve, and strengthen the mycelium material by way of liquid chemistry treatment such that it behaves and perform akin to an animal leather, common industrialized animal skin, or the like. Moreover, such a system and method would provide a unique molecular structure liquid chemistry treated fungal mat having variable shape, thickness, density, flexibility, and other predetermined qualities for industrial applications. Such a system and method for liquid chemistry treatment of fungal material would enhance the desired characteristics such as improved flexibility and tensile strength of the fungal material. Moreover, such a method would modify the structure or chemical composition, of the fungal material thereby conferring physical qualities according to the desired application. Such a method would utilize a unique molecular structure of liquid chemistry treated chitin-based fungal materials and their composites. Further, such a system and method would provide a liquid chemistry treated fungal biopolymer-based fungal mat for use in functional products. Moreover, such a system would provide a material that can act as an analog to synthetic plastic materials, foams, and animal skins. The present embodiment overcomes shortcomings in the field by accomplishing these critical objectives.

SUMMARY OF THE DISCLOSURE

To minimize the limitations found in the prior art, and to minimize other limitations that will be apparent upon the reading of the specification, the present application provides a system and a method for applying liquid chemistry to fungal materials and objects with variable shape, size, thickness, density, flexibility, and other predetermined qualities through post-growth processing in which thorough and complete chemical distribution is achieved. The present application provides a liquid chemistry treated, fungal composite with multiple unique aesthetic and performance features.

Certain embodiments of the present invention provides a method for liquid chemical treatment of a fungal material that was originally comprised predominately of fungal tissues. The resultant material is a flexible, optically homogenous, tunable density amorphous polymer that can serve in applications that are currently served by synthetic plastics as well as animal skins. As is known in the art, liquid chemistry treatment allows for control of many useful fungal properties, including mechanical properties such as tensile strength, tear strength, abrasion resistance and other chemical properties such as dye fixation.

The method of making a liquid chemistry treated biopolymer-based fungal material called fungal mat includes a ten step process. The method comprises the steps of: harvesting a plurality of fresh mycelium material from a substrate inoculated with a fungal tissue and marking each of the plurality of mycelium material for identification. Then, weighing and recording the initial mass of each of the plurality of mycelium material. Next, preparing a liquid chemical solution using solvent: chemical ratios from 0:100 to 100:0 and temperatures ranging from 10-60 degrees Celsius and decanting the liquid chemical solution into a vacuum tumbler drum. Distributing at least one of the plurality of mycelium material across the vacuum tumbler drum and applying vacuum to the vacuum tumbler drum to pull open the porous mycelium structure and to facilitate chemical ingress therethrough. Then, rotating the vacuum tumbler drum to ensure thorough mixing and refreshing of the liquid chemical solution at the mycelium surface and to prevent stagnant surface layer chemical concentrating on the mycelium surface. Thereafter, repeatedly vacuuming and rotating the vacuum tumbler drum and determining the extent of the liquid chemical solution uptake by the mycelium material to form at least one fungal mat. Finally, removing the at least one fungal mat from the vacuum tumbler drum, draining away surface moisture, and drying the at least one fungal mat.

At a macroscopic level, the method provides for an optically and chemically homogenous treated fungal mat. At a microscopic scale, the method may imbue a variety of chemical rearrangements upon the fungal materials, producing a more chemically homogenized fungal mat.

The system for making a biopolymer-based fungal mat, comprises a plurality of fresh fungal material, a marking means for marking each of the plurality of fungal material, a mass balance for weighing the initial masses of each of the plurality of fungal material, a liquid chemical solution for applying onto the plurality of fungal material and a vacuum tumbler drum adaptable to enclose at least one of the plurality of fungal materials and the liquid chemical solution. The tumbling action of the vacuum tumbler drum in combination with the vacuum applied causes the liquid chemical solution provided inside the vacuum tumbler drum to be continually drawn in and out of the mycelium material, inside the vacuum tumbler drum, thereby delivering superior chemical solution distribution on the fungal material producing a biopolymer-based fungal mat.

A first objective of the present embodiment is to provide a biopolymer-based fungal mat with well controlled mechanical and chemical properties.

A second objective of the present embodiment is to provide a method that can successfully alter, preserve, and strengthen a fungal material by way of liquid chemistry treatment such that it behaves and perform akin to an animal leather, common industrialized animal skin, or the like.

A third objective of the present embodiment is to provide a unique molecular structure liquid chemistry treated fungal mat having variable shape, thickness, density, flexibility, and other predetermined qualities for industrial applications.

Yet another objective of the present embodiment is to provide a system and method for liquid chemistry treatment of fungal material that enhances desired characteristics such as improved flexibility and tensile strength.

Yet another object of the present embodiment is to provide a method for liquid chemistry treatment for fungal materials that can modify the structure or chemical composition, of the fungal material thereby conferring physical qualities according to the desired application.

Yet another object of the present embodiment is to provide a liquid chemistry treated fungal biopolymer-based fungal mat for use in functional products.

Yet another object of the present embodiment is to provide a material that can act as an analog to synthetic plastic materials, foams, and animal skins.

These and other advantages and features of the present invention are described with specificity so as to make the present invention understandable to one of ordinary skill in the art.

BRIEF DESCRIPTION OF THE DRAWINGS

In order to enhance their clarity and improve the understanding of the various elements and embodiment shown herein, the figures have not necessarily been drawn to scale. Furthermore, elements that are known to be common and well understood to those in the industry are not depicted in order to provide a clear view of the various embodiments of the invention, thus the drawings are generalized in form in the interest of clarity and conciseness.

DETAILED DESCRIPTION OF THE DRAWINGS

In the following discussion that addresses a number of embodiments and applications of the present invention, reference is made to the accompanying drawings that form a part hereof, and in which is shown by way of illustration specific embodiments in which the invention may be practiced. It is to be understood that other embodiments may be utilized, and changes may be made without departing from the scope of the present invention.

Various inventive features are described below that can each be used independently of one another or in combination with other features. However, any single inventive feature may not address any of the problems discussed above or only address one of the problems discussed above. Further, one or more of the problems discussed above may not be fully addressed by any of the features described below.

As used herein, the singular forms "a", "an" and "the" include plural referents unless the context clearly dictates otherwise. "And" as used herein is interchangeably used with "or" unless expressly stated otherwise. As used herein, the term 'about" means +/−5% of the recited parameter. All embodiments of any aspect of the invention can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "wherein", "whereas", "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

Figure 1:
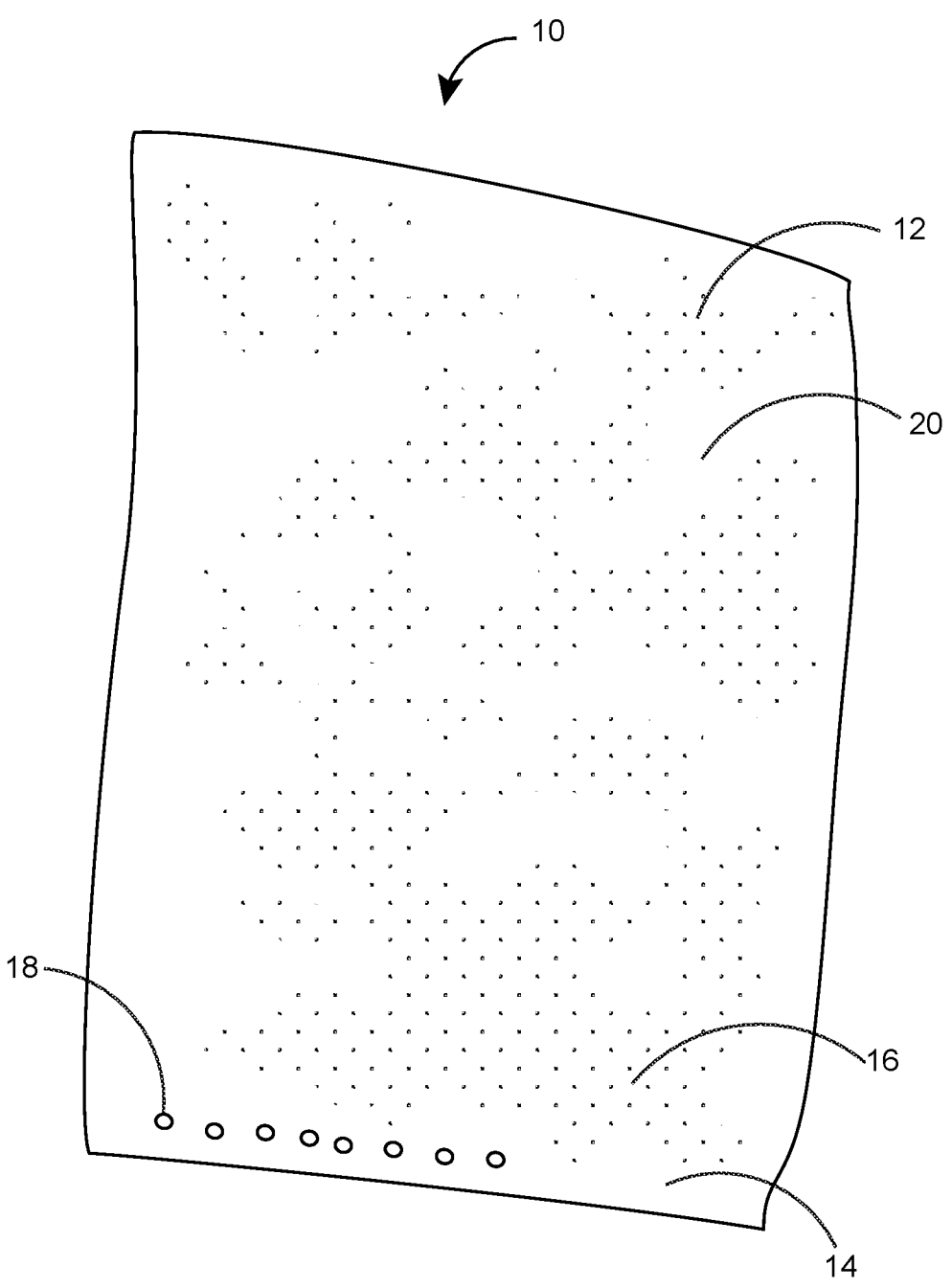
FIG. 1 illustrates a standard liquid chemistry treated biopolymer-based fungal mat in accordance with the preferred embodiment of the present invention.

The base inoculum and growth conditions used to produce the pre-liquid chemistry treated fungal material (the pre-liquid chemistry treated mycelium material) may be varied. The post-liquid chemistry treated fungal material (mycelium material) called fungal mat 10 is shown in FIG. 1. Exemplary growth conditions for the fungal materials are provided below (See "Fungal Materials" section below). The base inoculum is comprises a fungal inoculum, the fungal inoculum prepared from a desired fungi strain. In some embodiments, the desired fungal strain can include any vegetative, sexual, or asexual structure of a fungus that is capable of growing a new fungal colony. Notably, regardless of the starting materials, liquid chemistry treatment allows for control of many useful fungal properties, including mechanical properties such as tensile strength, tear strength, abrasion resistance and other chemical properties such as dye fixation.

As described above, the present application provides a system and method for liquid chemistry treatment of a fungal material that was comprised predominately of fungal tissues in its pre-liquid chemistry treated form. The fungal material of the present embodiment is mycelium material. Referring to FIG. 1, a standard liquid chemistry treated biopolymer-based fungal mat 10 (also referred to herein as "fungal mat swatch" or "swatch") is illustrated in its post-liquid chemistry treated form. The method for making the liquid chemistry treated fungal mat 10 includes a ten step process. The liquid chemistry treated fungal mat 10 includes markings 18 oriented along a proximal end 14, the proximal end 14 opposite a distal end 12. In some embodiments, the liquid chemistry treated fungal mat 10 includes uniformly translucent regions 20. The optical density, tensile strength, and other characteristics of the liquid chemistry treated fungal mat 10 can be variably optimized at various steps of the ten step preparation method 100 described below. In other embodiments, the liquid chemistry treated fungal mat 10 includes regions of darker pigmentation 16, permitting users to mimic the appearance of various leathers and hides in a temporally and spatially controlled manner.

As shown in FIG. 1, there are portions of the fungal mat 10 with higher opacity and higher translucency than other portions. The biopolymer-based fungal mat 10 is not transparent, but does exhibit a degree of transparency that is similar throughout the material and across its surface area. As a result of the process described herein, the fungal mat 10 has substantially the same opacity, texture and appearance in various portions of the fungal mat 10 that are pointed to by various reference numerals 12, 14 and 20.

In an exemplary embodiment, if the example fungal mat 10 shown in FIG. 1 is considered broken into even squares, for instance 4 squares, 16 squares or 64 squares, each square has an opacity, translucency and transparency value that can be measured. Because the solid fungal mat 10 is not perfectly opaque, part of the light hitting the solid fungal mat 10 penetrates its surface where internal scattering and lateral diffusion occurs away from the entry point. This lateral diffusion means the reflectivity of the translucent solid decreases with the size of the sample being tested. Thus, it is important to measure similar sample sizes across the surface area of the fungal mat 10 (such as the surface area of the side shown in FIG. 1). In the present process, the translucency, transparency and opacity of one even square may individually, or each together be within 5% of the value of all other squares in the sample, or within 5% of the total translucency, transparency and opacity of the entire sample taken as a whole. In other embodiments, the translucency, transparency and opacity values are within 10%, within 15%, within 25%, within 40%, or within 60% of the value of all other squares in the sample, or within 5% of the total translucency, transparency and opacity of the entire sample taken as a whole.

Figure 2:
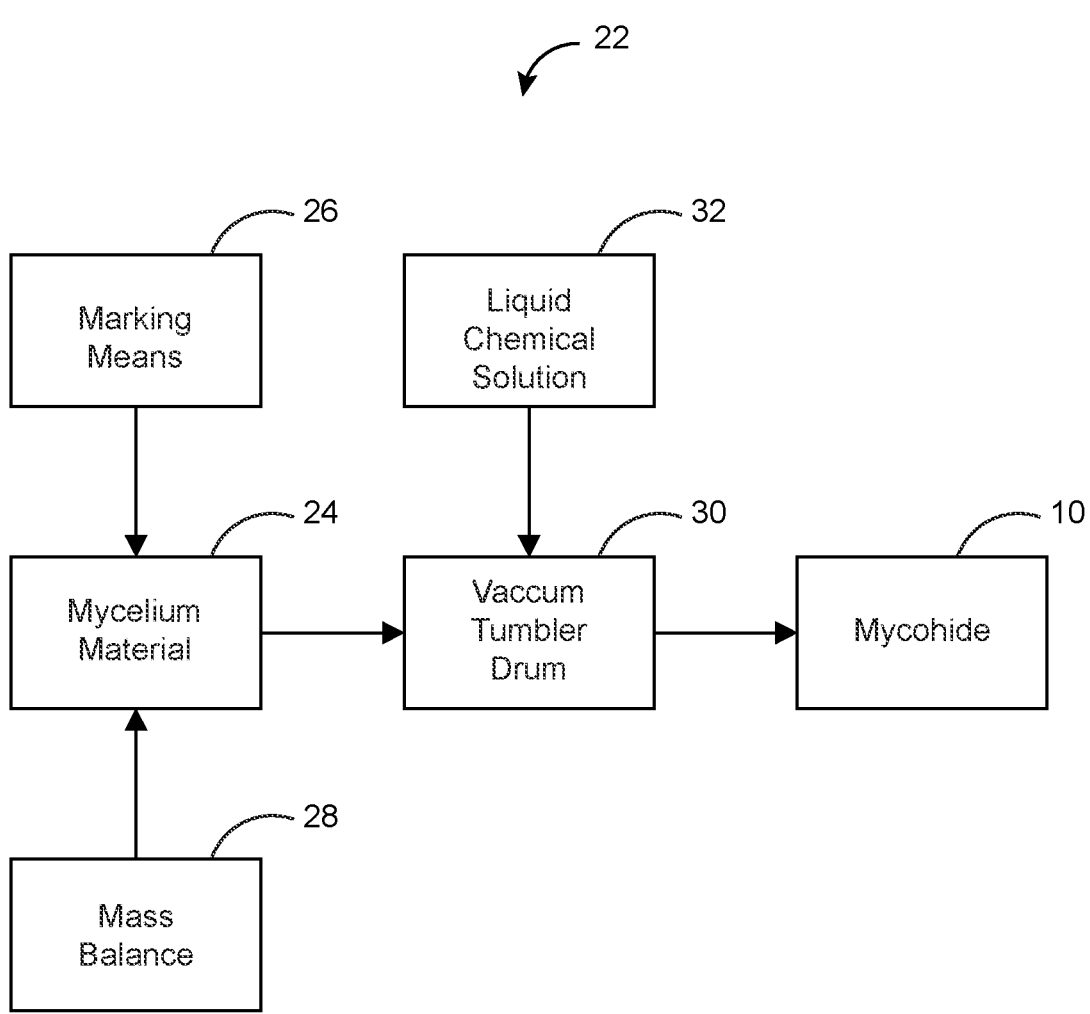
FIG. 2 illustrates a block diagram of a system employed for making the liquid chemistry treated biopolymer-based fungal mat in accordance with the preferred embodiment of the present invention.

FIG. 2 illustrates a block diagram of a system 22 employed for making the liquid chemistry treated biopolymer-based fungal mat 10 in accordance with the preferred embodiment of the present invention. The system 22 comprises a plurality of fresh mycelium material 24, a marking means 26 for marking each of the plurality of mycelium material 24, a mass balance 28 for weighing the initial masses of each of the plurality of mycelium material 24, a liquid chemical solution 32 for applying onto the plurality of mycelium material 24 and a vacuum tumbler drum 30 adaptable to enclose at least one of the plurality of mycelium material 24 and the liquid chemical solution 32 together. The marking means 26 allows marking of each of the plurality of mycelium material 24 and thereby allows tracking of data relative to each of the plurality of mycelium material 24. Weighing the initial mass of each of the plurality of mycelium material 24 with the mass balance 28 allows quantification of the mass of chemicals retained in the fungal mat 10 after drying. When the liquid chemical solution 32 is decanted into the vacuum tumbler drum 30 along with the plurality of mycelium materials 24, the tumbling action of the vacuum tumbler drum 30 in combination with the vacuum applied causes the liquid chemical solution 32 provided inside the vacuum tumbler drum 30 to be continually drawn in and out of the mycelium material 24, inside the vacuum tumbler drum 30, thereby delivering superior chemical solution distribution on the mycelium material 24 producing a biopolymer-based fungal mat 10.

Figure 3:
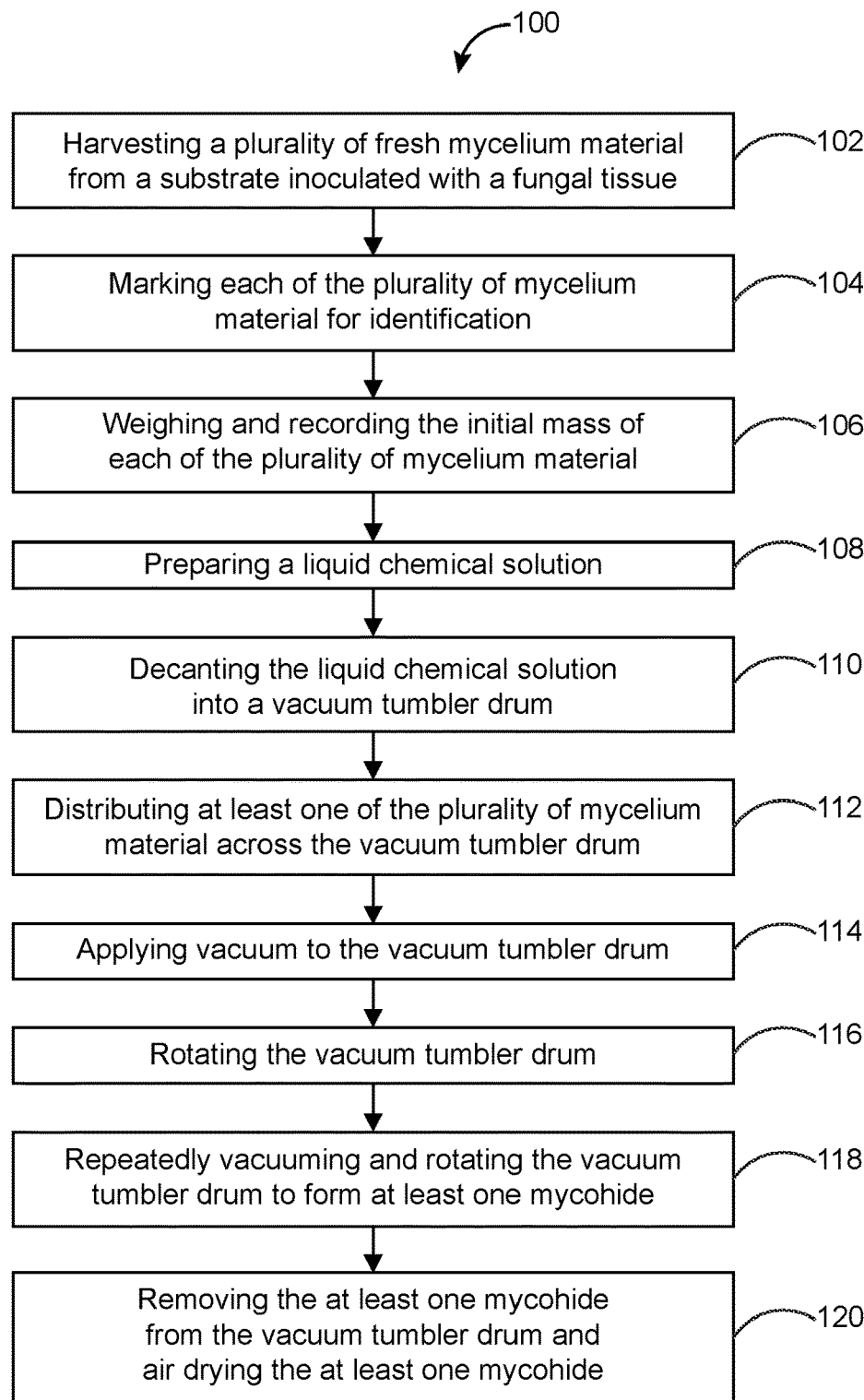
FIG. 3 illustrates a method for making the liquid chemistry treated biopolymer-based fungal mat in accordance with the preferred embodiment of the present invention.

FIG. 3 illustrates a method 100 for making the liquid chemistry treated biopolymer-based fungal mat 10 in accordance with the preferred embodiment of the present invention. The preferred method 100 of making liquid chemistry treated fungal mat 10 includes a ten step process wherein a plurality of fresh mycelium material 24 is transmuted into a liquid chemistry treated fungal mat 10. The method comprises the steps of: harvesting a plurality of fresh mycelium material from a substrate inoculated with a fungal tissue, as indicated at block 102, and marking each of the plurality of mycelium material for identification, as indicated at block 104. Then, as indicated at block 106, weighing and recording the initial mass of each of the plurality of mycelium material. Next, preparing a liquid chemical solution using solvent: chemical ratios from 0:100 to 100:0 and temperatures ranging from 10-90 degrees Celsius or from 10-60 degrees Celsius, as indicated in block 108 and decanting the liquid chemical solution into a vacuum tumbler drum, as indicated at block 110. Then, distributing at least one of the plurality of mycelium material across the vacuum tumbler drum, as indicated at block 112 and applying vacuum to the vacuum tumbler drum to pull open the porous mycelium structure and to facilitate chemical ingress therethrough, as indicated at block 114. Then, rotating the vacuum tumbler drum to ensure thorough mixing and refreshing of the liquid chemical solution at the mycelium surface and to prevent stagnant surface layer chemical concentrating on the mycelium surface, as indicated at block 116. After that, repeatedly vacuuming and rotating the vacuum tumbler drum and determining the extent of the liquid chemical solution uptake by the mycelium material to form at least one fungal mat, as indicated at block 118. Finally, as indicated at block 120, removing the at least one fungal mat from the vacuum tumbler drum, draining away surface moisture, and drying the at least one fungal mat.

At a macroscopic level, the liquid chemical treatment method 100 of the present application provides for an optically homogenous liquid chemically treated fungal mat 10. At a microscopic scale, the method imbues a variety of chemical rearrangements upon the mycelium materials 24, producing a more chemically homogenized product named fungal mat 10.

As an example, a two-swatch preparation of the fungal mat 10 can be considered, to facilitate the explanation of these ten steps of the method 100 in detail below. As indicated at block 102 of FIG. 3, the first step includes harvesting the plurality of mycelium material 24. In the exemplary embodiment, in the first step of the preferred method of making liquid chemistry treated fungal mat 10, two six inch by four inch swatches of fresh mycelium material 24 are cut to create a proximal end 14 and a distal end 12 with shears known in the art. In one embodiment, a 30 cm diameter small scale stainless steel dye drums are used, in which the subsequent wet processes can be carried out. In other embodiments, other optimization schemes are contemplated including size maximization, strength maximization, and/or vacuum tumbler drum output maximization per unit.

The second step, as indicated in block 104 of FIG. 3, includes marking each of the plurality of mycelium material 24 for identification utilizing the marking means 26. The marking means 26 allows marking of each of the plurality of mycelium material 24 and thereby tracking of data relative to each of the plurality of mycelium material 24. In one embodiment, a user can create punch holes in the plurality of mycelium material 24 for identification that permits the tracking of data relative to each of the plurality of mycelium material 24. In some embodiments, a variety of identification methods are contemplated, including a simple heat-branded insignia, an RFID tag, numeric identification, barcodes, and the like. In some embodiments, the punch holes along the proximal end 14 can be optically read by a sensor, permitting the automated identification and tracking of any given fungal material.

The third step in the exemplary embodiment of making liquid chemistry treated fungal mat 10, requires the user to weigh both swatches of mycelium material and record their initial masses utilizing the mass balance 28. The mass balance 28 is utilized to assay uptake of chemicals, permitting quantification of the mass of chemicals retained after drying. Alternately a variety of methods may be employed to provide such quantification, including MALDI-Mass Spectrometry, Nuclear Magnetic Resonance, the analysis of levo-rotary plane polarized light, and the like.

As shown in block 108 of FIG. 3, in a fourth step, a liquid chemical solution 32 is prepared. Specifically, in the preferred example, three kilograms of liquid chemical solution is prepared. This particular mass is utilized in the laboratory scale two-swatch approach at a potential pH range of 1.0-14.0, or more preferably 2.0-12.0 as it is known to achieve optimized movement and equilibration of the mycelium material 24, and further to optimize distribution of the liquid in the standard vacuum tumbler drum 30. Liquid chemical solutions are prepared using solvent: chemical ratios from 0:100 to 100:0 to achieve a total liquid chemical solution weight of 3000g and using temperatures of 10-90 or 10-60 degrees Celsius. The chemical is preferably added to liquid whilst stirring with a glass rod. The liquid chemical solution 32 utilized in the present embodiment can be any chemical solution that requires vacuum treatment methodology to achieve penetration and distribution. Some examples of the liquid chemical solutions that can function as plasticization/fatliquoring, dyeing, washing, acidifying, basifying, tanning, retanning, filling, degreasing, reactions in polar solvents, reaction in non-polar solvents, enzymatic/ biological reactions and bleaching can be used.

As shown in block 110 of FIG. 3, the fifth step in the preferred method of making liquid chemically treated fungal mat 10 involves decanting liquid chemical solution 32 into the vacuum tumbler drum 30. Specifically, the user removes the lid from vacuum tumbler drum 30 and subsequently pour the liquid chemical solution 32 into the vacuum tumbler drum 30. In some embodiments, the liquid chemical solution 32 is introduced into the vacuum tumbler drum 30 prior to addition of the mycelium material 24 to the vacuum tumbler drum 30. At scale, this ordering will prevent mycelium material 24 from self-adhering at the proximal 14 or distal ends 12 or at the flat interfaces, resulting in improved, liquid chemical distribution and access to all angles of the mycelium material 24. Notably tumbling action of the vacuum tumbler drum 30 creates a gentle flexing of the mycelium material 24 and a gentle mixing of liquid chemical solution 32. The flexing action of the porous mycelium material 24 in combination with the vacuum applied, causes liquid chemical solution 32 to be continually drawn in and out of the mycelium material 24 as it flexes, as well as being pumped by the flexing action throughout the mycelium matrix, delivering superior chemical solution distribution. The use of low drum rotation (0.5-10) RPM ensures that mycelium material 24 does not adhere to vacuum tumbler drum walls due to the action of centrifugal forces. Friction across self-adherent boundaries vary directly with the surface area of mycelium material 24 self-adhesion and inversely with the hydroscopy of the solubilizing solution.

As shown in block 112 of FIG. 3, the sixth step in the preferred method 100 involves distributing the mycelium material 24 across the vacuum tumbler drum 30. Specifically, in the preferred example, this involves placement of two weighed swatches of mycelium material 24 into the vacuum tumbler drum 30, one sample on each side of the perforated divider. The swatches of mycelium material 24 can be set down at either their proximal 14 or distal ends 12. In this example, the purpose of placing samples of mycelium material 24 on either side of the perforated divider is to eliminate or reduce sample self-adherence and to maximize distribution and access of the liquid chemical solution 32 to each sample of the mycelium material 24. For vacuum tumbler drums without perforated divider, the swatches are uniformly distributed within. As described above, the tumbling action of the vacuum tumbler drum 30 creates a centrifugal force that can be expressed as a velocity (m/s) or acceleration (m/s^2).

As shown in block 114 of FIG. 3, the seventh step of the preferred method 100 includes applying a vacuum to the vacuum tumbler drum 30. The preferred example requires replacing the lid of the vacuum tumbler drum 30, including manually screwing down the lid by hand. In some embodiments, there is no need to over-tighten the lid because a vacuum is applied. In some embodiments, the user ensures that the vacuum valve on top of lid remains open. Next, a vacuum hose is applied to the lid and a vacuum activator button is engaged by the user. The vacuum is applied in the vacuum tumbler drum 30 until it reaches the target vacuum level per the digital display/dial. Next, the vacuum valve is closed and the vacuum hose is disconnected. Thus, a vacuum is applied to pull open the porous mycelium structure, facilitating chemical ingress.

As shown in block 116 of FIG. 3, the eighth step in the preferred method 100 includes rotating the vacuum tumbler drum 30 to ensure thorough mixing and refreshing of the liquid chemical solution 32 at the mycelium surface and to prevent stagnant surface layer chemical concentrating on the mycelium surface. In the example, the eighth step requires placing the vacuum tumbler drum 30 on the rotator platform. Next, the user selects the run time (in minutes) and desired rotational speed (in vacuum tumbler with variable speed control) engages the start button in order to begin rotation of the vacuum tumbler drum 30. Notably, this mechanical rotation of the vacuum tumbler drum 30 ensures thorough mixing and refreshing of the liquid chemical solution 32 at mycelium surface and at the proximal 14 or the distal ends 12, such that no stagnant surface layer chemical concentrations are established. As described above, notably the tumbling action of the vacuum tumbler drum 30 creates a gentle flexing of the mycelium material 24 and a gentle mixing of liquid chemical solution 32. The flexing action of the porous mycelium material 24 in combination with the vacuum applied, causes liquid chemical solution 32 to be continually drawn in and out of the mycelium material 24 as it flexes, as well as being pumped by the flexing action throughout the mycelium matrix, delivering distribution of superior liquid chemical solution 32. The use of low vacuum tumbler drum rotation RPM (0.5-10) ensures that mycelium material 24 does not adhere to the vacuum tumbler drum walls due to the action of centrifugal forces.

As indicated at in block 118 of FIG. 3, the ninth step of the preferred method 100 includes repeatedly vacuuming and rotating the vacuum tumbler drum 30 and determining the extent of the liquid chemical solution 32 uptake by the mycelium material 24 to form at least one fungal mat 10. In the preferred example, the ninth step involves running the vacuum tumbler drum 30 for a desired duration (for example, thirty minutes), then determining the extent of liquid chemistry solution 32 uptake by removing thus formed fungal mat 10.

As indicated at block 120 of FIG. 3, the tenth step of the method 100 includes removing the at least one fungal mat 10 from the vacuum tumbler drum 30, draining away surface moisture, and drying the at least one fungal mat 10. In the exemplary embodiment, the process of removing the fungal mat 10 by their proximal 14 or distal ends 12 is followed by dabbing away surface/excess liquid using paper towels, and weighing the fungal mat 10. In some embodiments, this process is continued until two consecutive fungal mat weight measurements are equal (i.e., weight increase against time has plateaued). The fungal mat can be manipulated at set down at the either their proximal 14 or distal ends 12.

In some embodiments of the tenth step, the running time for the vacuum tumbler drum 30 can be automatically set to stop to allow process intervention. In other embodiments, thirty minutes is used as a convenient interval to take weight measurements. As described above, the weight measurements are plotted against time in order to track the extent of liquid chemical uptake. Notably, in some embodiments, weight increase alone can be utilized to assay the completeness of liquid chemical uptake. In some embodiments, percentage translucence of the samples is monitored by way of various methods established in the field, including optical density measurement, and light intensity measurement.

Notably, dried fibers can be readily and uniformly rehydrated prior to the above-described aqueous steps, resulting in improved mycelium availability for downstream aqueous chemical interactions. The result is softer product that is less prone to cracking than similar materials known in the art.

The tenth step in the preferred method 100 of making liquid chemistry treated fungal mat 10 requires removing fungal mat 10 from the vacuum tumbler drum 30, dabbing away surface moisture, and drying the fungal mat 10. In some embodiments, drying of fungal mat 10 continues for at least four days. After drying, the fungal mat 10 is weighed and assayed for moisture content. Notably, obtaining weight and moisture content measurements in this manner allows the user to track the final extent of liquid chemical treatment over time, with the weight increase largely attributable to the action of the chemical. The fungal mat 10 can be manipulated by their proximal 14 or distal ends 12 as described above. Finally, the liquid chemistry treated fungal mat 10 is manually dried prior to shipping. This final part of the tenth step minimizes or inhibits any remaining biological activity within the liquid chemistry treated fungal mat 10 that might otherwise continue at basal levels during transit.

In some embodiments, liquid chemistry treated fungal mat 10 may also include a region of darker pigmentation 16 (also known as "non-translucent areas"). These non-translucent areas of the sheet are comprised of particularly dense mycelium fiber regions. In some embodiments, penetration with liquid chemicals during vacuum treatment can cause these regions of darker pigmentation 16 to appear translucent, hence the percentage translucent area increases with time as the vacuum liquid chemistry treatment progresses. Notably, drying any dense areas that have not been penetrated by liquid chemistry may contain self-adhering mycelium fibers. Following water spot testing, the mycelium fibers may become more hydrophobic. In some embodiments, after these dense areas are penetrated by liquid chemistry, they become more translucent and more hydrophilic.

As described above, the liquid chemically treated fungal mat 10 includes uniformly translucent regions 20 derived from a unique ten step preparation method 100. Notably, the finished fungal mat 10 has a more uniform translucency than would be expected from a typical sheet of mycelium known in the art. The translucency is qualitatively observed by the passage of light through a given fungal mat at a uniform intensity to a viewer. Alternately, translucency can be empirically measured with an optical density measuring device, for example by the homogenous measurement of 95% to 100% intensity of light passage through the given fungal mat 10. A light box can also be utilized to control light intensity, viewing angle, and illumination intensity.

Referring to FIG. 1, a standard liquid chemistry treated fungal mat 10 is translucent to light, optically heterogeneous at its various ends, and adaptable to a variety of sizes, shapes, and rigidities. In one example, following the ten step process 100 of harvesting, marking, weighing, preparing a chemical solution, vacuuming, drying, and the like, a singular large sheet of liquid chemistry treated product is produced. In this example, depending on the volume of the vacuum tumbler drum 30, the proximal end 14 can extend from ten to five hundred inches, the distal end 12 can extend from ten to five hundred inches, with the markings 18 at the proximal end 14 extending from the left aspect for ten to five hundred inches, or any desired variations of those lengths. In some embodiments, the liquid chemically treated fungal mat 10 in this example includes uniformly translucent regions 20 in addition to regions of darker pigmentation 16, permitting users to mimic the appearance of various leathers and hides at a very large scale.

In another example, following the ten step process 100 of harvesting, marking, weighing, preparing a liquid chemical solution, vacuuming, drying, and the like, a medium-sized sheet of plasticized product is produced. A standard medium-sized liquid chemistry treated fungal mat 10 is also translucent to light, optically heterogeneous at its various ends, and adaptable to a variety of sizes, shapes, and rigidities. In this example, depending on the volume of the vacuum tumbler drum 30, the proximal end 14 can extend from ten to five hundred inches, the distal end 12 can extend from ten to five hundred inches, with the markings 18 of the proximal end 14 extending from the left aspect for two to ten inches, or any desired variations of those lengths. In some embodiments, the liquid chemistry treated fungal mat 10 in this example includes uniformly translucent regions 20 in addition to regions of darker pigmentation 16, permitting users to mimic the appearance of various leathers and hides at a medium-sized scale.

In yet another example, following the ten step process 100 of harvesting, marking, weighing, preparing a liquid chemistry solution, vacuuming, drying, and the like, a small-sized sheet of liquid chemistry treated fungal mat 10 is produced. A standard small-sized liquid chemistry treated fungal mat 10 is also translucent to light, optically heterogeneous at its various ends, and adaptable to a variety of sizes, shapes, and rigidities, yet it is also capable of being stitched together into various shapes and sizes like a quilt. In this example, depending on the volume of the vacuum tumbler drum 30, the proximal end 14 can extend from two to ten inches, the distal end 12 can extend from two to ten inches, with the markings 18 of the proximal end 14 extending from the left aspect for about one to two inches, or any desired variations of those lengths. In some embodiments, the liquid chemistry treated fungal mat 10 in this example includes uniformly translucent regions 20 in addition to regions of darker pigmentation 16, permitting users to mimic the appearance of various leathers and hides at a small-sized scale.

Fungal Materials

As described above, the present invention provides a system 22 and method 100 for applying liquid chemicals to a fungal material that was originally comprised predominately of fungal tissues. The origins of this initial fungal material comprises the pre-liquid chemistry treated mycelium material. In the preferred embodiment, the mycelium material 24 is propagated from a colonizable substrate that has been inoculated with fungi. Preferred species include the Ganodermas, the order Polyporales generally, and including all saprobic fungal candidates that derive sustenance from lignin and cellulose-rich sources.

Below is provided an example of pre-liquid chemistry treated mycelium growth conditions. First, a fungal inoculum may be introduced into a substrate within an enclosure or prior to being introduced to the enclosure so as to provide an even distribution of fungus throughout. Next, the substrate is left to colonize. An intermediate layer is established on an open surface of the colonized substrate to control the interaction of the forming fungal tissue structure with the substrate. The presence of a uniform intermediate material atop the substrate enables a consistent surface from which the fungal tissues may grow, supporting uniform expansion of the fungal hyphae into the environment, and providing a determined space for manipulation by chemical and physical controls. Live fungal hyphae grow from the substrate and through the intermediate layer. In some instances, the living tissues that extend through the intermediate layer are manipulated to achieve a material having a desired thickness, shape, size and qualities.

Next, the intermediate layer may be delaminated from the nutrient source out of which it has grown to terminate further growth of the material, or the fungal tissue layer may be delaminated from the intermediate layer, which is left in place and optionally reused. The resultant living fungal tissue structures may optionally be fused with other living fungal tissue structures to create two-dimensional and three-dimensional structures. The final fungal tissue may then be subjected to post-growth processing to achieve desired properties for downstream usage.

The fungal substrate precursor material ("pre-liquid chemistry treated fungal mat") may be cultivated in either batch or continuous processes and the fungal tissues may be modified and directed during growth in order to achieve uniform characteristics across a surface or be engineered to take on distinct local qualities through manipulation of growing tissue, or the addition of particles, fibers, meshes, fabrics, and other additives, armatures, and components. Fungal tissue sheets may be processed via cutting or other forming methods to obtain two-dimensional features and reliefs, or individual sheets may be stacked and grown together to form three-dimensional features or composed with reinforcements or other structural amendments that may be incorporated into a growing tissue.

In some embodiments, liquid chemistry treated fungal materials described herein can behave and perform akin to an animal leather, common industrialized animal skin, or the like. This may be achieved based on the unique molecular structure of liquid chemistry treated chitin-based fungal materials and their composites. In some embodiments, post-processing of liquid chemistry treated fungal materials may be used to modify its structure or chemical composition, thereby conferring physical qualities according to desired applications.

The foregoing description of the preferred embodiment of the present invention has been presented for the purpose of illustration and description. It is not intended to be exhaustive or to limit the invention to the precise form disclosed. Many modifications and variations are possible in light of the above teachings. It is intended that the scope of the present invention to not be limited by this detailed description, but by the claims and the equivalents to the claims appended hereto.

What is claimed is:

1. A method for making a biopolymer-based fungal mat, comprising:

harvesting a plurality of fresh fungal materials from a substrate inoculated with a fungal tissue;

marking each of the plurality of fresh fungal materials for identification by creating a plurality of punch holes oriented along a proximal end of each of the plurality of fresh fungal materials;

weighing and recording initial masses of each of the plurality of fresh fungal materials using a mass balance;

providing a liquid chemical solution having a solvent-to-chemical ratio from 0:100 to 100:0 and temperatures ranging from 10° C. to 60° C.;

decanting the liquid chemical solution into a vacuum tumbler drum;

distributing at least one of the plurality of fresh fungal materials across the vacuum tumbler drum on respective sides of a perforated divider disposed within the vacuum tumbler drum, the perforated divider being configured to permit flow of the liquid chemical solution while reducing self-adherence among the at least one of the plurality of fresh fungal materials;

sealing the vacuum tumbler drum and applying vacuum to the vacuum tumbler drum to pull open a porous fungal structure of the at least one of the plurality of fresh fungal materials and to facilitate ingress of the liquid chemical solution therethrough;

rotating, using variable speed control, the vacuum tumbler drum at a rotational speed between 0.5 and 10 RPM to ensure thorough mixing and refreshing of the liquid chemical solution at a surface of the at least one of the plurality of fresh fungal materials and to prevent stagnant surface layer chemical concentration on the surface of the at least one of the plurality of fresh fungal materials;

repeatedly vacuuming and rotating the vacuum tumbler drum thereby providing liquid chemical solution uptake by the at least one of the plurality of fresh fungal materials to form the biopolymer-based fungal mat; and removing the biopolymer-based fungal mat from the vacuum tumbler drum, draining away surface moisture thereon, and drying the biopolymer-based fungal mat to provide a dried fungal mat, the dried fungal mat including uniformly translucent regions.

2. The method of claim 1 wherein weighing the initial mass of each of the plurality of fresh fungal materials with the mass balance allows quantification of a mass of chemicals retained in the fungal mat after drying.

3. The method of claim 1 wherein the plurality of fresh fungal materials comprises mycelium.

4. The method of claim 1 wherein repeatedly vacuuming and rotating the vacuum tumbler drum comprises, for each cycle, applying vacuum to a target vacuum level indicated by a display or dial associated with the vacuum tumbler drum and rotating the vacuum tumbler drum for a user-selected run time.

5. The method of claim 1, further comprising optically reading the plurality of punch holes using a sensor, thereby permitting an automated identification and tracking of the plurality of fresh fungal materials.

* * * * *